(12) United States Patent
Huang et al.

(10) Patent No.: US 11,071,466 B2
(45) Date of Patent: Jul. 27, 2021

(54) PORTABLE DEVICE AND BLOOD PRESSURE MEASUREMENT METHOD

(71) Applicant: BOE TECHNOLOGY GROUP CO., LTD., Beijing (CN)

(72) Inventors: Zicheng Huang, Beijing (CN); Liang Li, Beijing (CN); Pan Ni, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 309 days.

(21) Appl. No.: 16/019,948

(22) Filed: Jun. 27, 2018

(65) Prior Publication Data
US 2019/0059751 A1    Feb. 28, 2019

(30) Foreign Application Priority Data

Aug. 24, 2017  (CN) .......................... 201710735692.8

(51) Int. Cl.
*A61B 5/02*          (2006.01)
*A61B 5/021*         (2006.01)
(Continued)

(52) U.S. Cl.
CPC ........ *A61B 5/02108* (2013.01); *A61B 5/1172* (2013.01); *A61B 5/332* (2021.01);
(Continued)

(58) Field of Classification Search
CPC ............ A61B 5/02125; A61B 5/02108; A61B 5/1172; A61B 5/0404; A61B 5/6898; A61B 5/04028; A61B 5/6826; A61B 5/7278
See application file for complete search history.

(56) References Cited

U.S. PATENT DOCUMENTS

2011/0058091 A1*  3/2011  Hsu .................. G06K 9/0004
                                              348/340
2012/0071734 A1   3/2012  Shimuta et al.
(Continued)

FOREIGN PATENT DOCUMENTS

CN       102058400 A     5/2011
CN       102413761 A     4/2012
(Continued)

OTHER PUBLICATIONS

First Office Action for Chinese Application No. 201710735692.8, dated Oct. 12, 2019, 15 Pages.

*Primary Examiner* — Navin Natnithithadha
*Assistant Examiner* — Andrey Shostak
(74) *Attorney, Agent, or Firm* — Brooks Kushman P.C.

(57) ABSTRACT

A portable device includes: an ECG detection circuitry configured to detect an ECG signal of a user; a pulse detection circuitry configured to detect a pulse wave signal of the user; an identity determination circuitry configured to determine identity information about the user; and a blood pressure calculation circuitry connected to the ECG detection circuitry, the pulse detection circuitry and the identity determination circuitry, storing therein a plurality of blood pressure calculation models, and configured to select a blood pressure calculation model corresponding to the identity information about the user among the plurality of blood pressure calculation models in accordance with the identity information, and perform calculation to acquire a blood pressure signal of the user using the selected blood pressure calculation model in accordance with the ECG signal and the pulse wave signal.

12 Claims, 3 Drawing Sheets

(51) Int. Cl.
  *A61B 5/00* (2006.01)
  *A61B 5/1172* (2016.01)
  *A61B 5/332* (2021.01)
  *A61B 5/327* (2021.01)
(52) U.S. Cl.
  CPC ........ *A61B 5/6898* (2013.01); *A61B 5/02125* (2013.01); *A61B 5/327* (2021.01); *A61B 5/6826* (2013.01); *A61B 5/7278* (2013.01)

(56) References Cited

U.S. PATENT DOCUMENTS

| | | | | |
|---|---|---|---|---|
| 2014/0223531 | A1* | 8/2014 | Outwater | H04M 1/72519 726/7 |
| 2015/0182132 | A1* | 7/2015 | Harris | A61B 5/7282 340/870.01 |
| 2017/0193207 | A1* | 7/2017 | Ashley | G06F 21/32 |
| 2017/0202464 | A1* | 7/2017 | Tsao | A61B 5/02416 |
| 2017/0245767 | A1* | 8/2017 | Ferber | A61B 5/0285 |
| 2017/0249445 | A1* | 8/2017 | Devries | A61B 5/1455 |
| 2017/0311815 | A1* | 11/2017 | Yu | A61B 5/6826 |
| 2018/0005014 | A1* | 1/2018 | Chen | G06K 9/0002 |
| 2018/0140205 | A1* | 5/2018 | Matsumoto | A61B 5/04288 |
| 2018/0184921 | A1* | 7/2018 | Baxi | A61B 5/7278 |
| 2018/0263518 | A1 | 9/2018 | Shimuta | |
| 2018/0344193 | A1* | 12/2018 | Gui | A61B 5/02125 |
| 2019/0159723 | A1* | 5/2019 | Nakajima | A61B 5/7239 |

FOREIGN PATENT DOCUMENTS

| | | |
|---|---|---|
| CN | 103099611 A | 5/2013 |
| CN | 104323764 A | 2/2015 |
| CN | 104706348 A | 6/2015 |
| CN | 105748051 A | 7/2016 |
| CN | 106725392 A | 5/2017 |
| EP | 2289405 A1 | 3/2011 |
| WO | 2017086071 A1 | 5/2017 |

* cited by examiner

PORTABLE DEVICE AND BLOOD PRESSURE MEASUREMENT METHOD

CROSS-REFERENCE TO RELATED APPLICATION

This application claims priority to Chinese Patent Application No. 201710735692.8 filed on Aug. 24, 2017, which is incorporated herein by reference in its entirety.

TECHNICAL FIELD

The present disclosure relates to the field of blood pressure measurement technology, in particular to a portable device and a blood pressure measurement method.

BACKGROUND

Along with the improvement of the living standard, health issues, such as blood pressure being an important indicator of human health, have attracted more and more attentions. Currently, there are various sphygmomanometers for detecting the blood pressure, including mercury sphygmomanometer and electronic sphygmomanometer. Although these sphygmomanometers are capable of meeting the blood pressure detection requirement, they are inconvenient to carry, and a detection result thereof is not sufficiently accurate.

SUMMARY

In one aspect, the present disclosure provides in some embodiments a portable device, including: an electrocardiogram (ECG) detection circuitry configured to detect an ECG signal of a user; a pulse detection circuitry configured to detect a pulse wave signal of the user; an identity determination circuitry configured to determine identity information about the user; and a blood pressure calculation circuitry connected to the ECG detection circuitry, the pulse detection circuitry and the identity determination circuitry, storing therein a plurality of blood pressure calculation models, and configured to select a blood pressure calculation model corresponding to the identity information about the user among the plurality of blood pressure calculation models in accordance with the identity information, and perform calculation to acquire a blood pressure signal of the user using the selected blood pressure calculation model in accordance with the ECG signal and the pulse wave signal.

In a possible embodiment of the present disclosure, the pulse detection circuitry includes: a light-emission sub-circuitry configured to generate an initial light signal; a photosensing sub-circuitry configured to collect a reflected light signal formed after the initial light signal is reflected by the user; and a first signal processing sub-circuitry connected to the photosensing sub-circuitry and configured to process the reflected light signal so as to acquire the pulse wave signal of the user.

In a possible embodiment of the present disclosure, the identity determination circuitry includes: a fingerprint identification sensor configured to determine fingerprint information about the user; and an inquiry sub-circuitry configured to inquire the identity information about the user in accordance with the fingerprint information about the user.

In a possible embodiment of the present disclosure, the portable device is a mobile terminal, a fingerprint identification button of the mobile terminal further serves as the fingerprint identification sensor, a flash lamp of the mobile terminal further serves as the light-emission sub-circuitry, and a camera of the mobile terminal further serves as the photosensing sub-circuitry.

In a possible embodiment of the present disclosure, the mobile terminal is a smart phone.

In a possible embodiment of the present disclosure, the initial light signal is a green light signal, a red light signal or an infrared light signal.

In a possible embodiment of the present disclosure, the ECG detection circuitry includes: an ECG detection electrode arranged on the portable device and configured to collect voltage signals corresponding to a left hand and a right hand of the user respectively; and a second signal processing sub-circuitry connected to the ECG detection electrode and configured to process the voltage signals corresponding to the left hand and the right hand of the user respectively, so as to acquire the ECG signal of the user.

In a possible embodiment of the present disclosure, the ECG detection electrode and a housing of the portable device are formed into one piece. The ECG detection electrode includes three ECG detection sub-electrodes insulated from each other. In the case that the portable device is used by the user to measure a blood pressure, one hand of the user is in contact with two of the three ECG detection sub-electrodes at a contact area greater than or equal to 1 cm$^2$, and the other hand of the user is in contact with the remaining one of the three ECG detection sub-electrodes.

In a possible embodiment of the present disclosure, the ECG detection electrode includes three ECG detection sub-electrodes arranged inside the portable device and insulated from each other. A housing of the portable device includes a first portion, a second portion and a third portion through which the voltage signals are capable of being transmitted. The first portion, the second portion and the third portion are insulated from each other and electrically connected to the three ECG detection sub-electrodes respectively.

In a possible embodiment of the present disclosure, the portable device further includes a behavior pattern detection circuitry connected to the blood pressure calculation circuitry and configured to detect behavior pattern information about the user during the measurement of the blood pressure of the user. The blood pressure calculation circuitry is further configured to modify the blood pressure signal of the user in accordance with the behavior pattern information.

In a possible embodiment of the present disclosure, the behavior pattern detection circuitry includes a movement sensor arranged on the portable device.

In a possible embodiment of the present disclosure, the behavior pattern information includes information indicating that the user is in a movement state, a sit-down state or a sleep state during the measurement of the blood pressure.

In a possible embodiment of the present disclosure, the portable device further includes a display circuitry configured to display the behavior pattern information, the ECG signal, the pulse wave signal, the identity information and/or the modified blood pressure signal.

In a possible embodiment of the present disclosure, the blood pressure calculation model is $BP=f(x,y)*h(a,b,c,d)$, where BP represents the blood pressure signal of the user, x represents the ECG signal of the user, y represents the pulse wave signal of the user, a represents gender of the user, b represents an age of the user, c represents a height of the user, and d represents a weight of the user.

In another aspect, the present disclosure provides in some embodiments a blood pressure measurement method for use in the above-mentioned portable device, including steps of: detecting an ECG signal of a user; detecting a pulse wave signal of the user; determining identity information about the user; and selecting a blood pressure calculation model corresponding to the identity information about the user among the plurality of blood pressure calculation models in accordance with the identity information, and performing calculation to acquire a blood pressure signal of the user using the selected blood pressure calculation model in accordance with the ECG signal and the pulse wave signal.

In a possible embodiment of the present disclosure, the blood pressure calculation model is $BP=f(x,y)*h(a,b,c,d)$, where BP represents the blood pressure signal of the user, x represents the ECG signal of the user, y represents the pulse wave signal of the user, a represents gender of the user, b represents an age of the user, c represents a height of the user, and d represents a weight of the user.

BRIEF DESCRIPTION OF THE DRAWINGS

The following drawings are provided to facilitate the understanding of the present disclosure, and constitute a portion of the description. These drawings and the following embodiments are for illustrative purposes only, but shall not be construed as limiting the present disclosure. In these drawings.

DETAILED DESCRIPTION

The present disclosure will be described hereinafter in conjunction with the drawings and embodiments, so as to further explain the portable device and the blood pressure measurement method according to the embodiments of the present disclosure.

Figure 1:
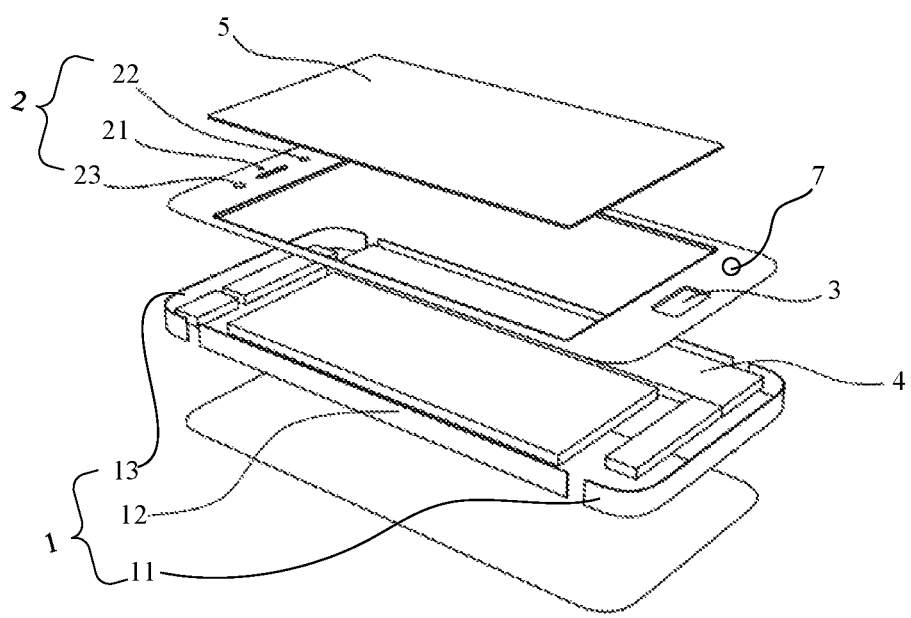
FIG. 1 is a schematic view showing a portable device according to one embodiment of the present disclosure.

As shown in FIG. 1, the present disclosure provides in some embodiments a portable device, including: an ECG detection circuitry 1 configured to detect an ECG signal of a user to be measured, wherein the ECG detection circuitry 1 may detect the ECG signal of the user in a single-channel or multi-lead manner; a pulse detection circuitry 2 configured to detect a pulse wave signal of the user; an identity determination circuitry 3 configured to determine identity information about the user, e.g., gender, age, height, weight and medical history; and a blood pressure calculation circuitry 7 connected to the ECG detection circuitry 1, the pulse detection circuitry 2 and the identity determination circuitry 3, storing therein a plurality of blood pressure calculation models, and configured to select a blood pressure calculation model corresponding to the identity information about the user among the plurality of blood pressure calculation models in accordance with the identity information, and perform calculation to acquire a blood pressure signal of the user using the selected blood pressure calculation model in accordance with the ECG signal and the pulse wave signal.

Specifically, the blood pressure calculation models may be created on the basis of different types of identity information (e.g., different blood pressure calculation models may be created with respect to a young user, an old user or a user with a medical history), such that the created blood pressure calculation models may meet the requirements on different types of identity information. Then, the created blood pressure calculation models may be stored in the blood pressure calculation circuitry 7. Upon the receipt of the identity information about the user, the blood pressure calculation circuitry 7 may select, from the pre-stored blood pressure calculation models, the blood pressure calculation model corresponding to the identity information about the user. In some embodiments of the present disclosure, each blood pressure calculation model may be a mathematical model for blood pressure calculation.

In the case that the above-mentioned portable device is adopted by the user to measure a blood pressure, the identity determination circuitry 3 may determine the identity information about the user, and transmit the determined identity information to the blood pressure calculation circuitry 7. The blood pressure calculation circuitry 7 may select, from the pre-stored blood pressure calculation models, the blood pressure calculation model corresponding to the identity information about the user in accordance with the identity information about the user. The ECG detection circuitry 1 may detect the ECG signal of the user, and transmit the detected ECG signal to the blood pressure calculation circuitry 7. The pulse detection circuitry 2 may detect the pulse wave signal of the user, and transmit the pulse wave signal to the blood pressure calculation circuitry 7. Then, the blood pressure calculation circuitry 7 may perform calculation to acquire the blood pressure signal of the user using the selected blood pressure calculation model in accordance with the ECG signal and the pulse wave signal.

Based on the above-mentioned structure of the portable device and the blood pressure measurement procedure implemented by the user using the portable device, the portable device includes the ECG detection circuitry 1, the pulse detection circuitry 2, the identity determination circuitry 3, and the blood pressure calculation circuitry 7 connected to the ECG detection circuitry 1, the pulse detection circuitry 2 and the identity determination circuitry 3. In the case that the blood pressure is measured by the user using the portable device, the identity determination circuitry 3 determines the identity information about the user, and transmits the determined identity information to the blood pressure calculation circuitry 7. The blood pressure calculation circuitry 7 selects the blood pressure calculation model corresponding to the identity information about the user in accordance with the identity information about the user. The ECG detection circuitry 1 and the pulse detection circuitry 2 detect the ECG signal and the pulse wave signal of the user respectively, and transmit the ECG signal and the pulse wave signal to the blood pressure calculation circuitry 7. Then, the blood pressure calculation circuitry 7 performs calculation to acquire the blood pressure signal of the user using the selected blood pressure calculation model in accordance with the ECG signal and the pulse wave signal. As a result, it is able for the user to carry the portable device conveniently and measure the blood pressure at any time and at any place if required. In addition, it is able to select the respective blood pressure calculation models corresponding to different users, thereby to provide a blood pressure detection result in a more accurate manner.

The pulse detection circuitry 2, the identity determination circuitry 3 and the ECG detection circuitry 1 of the portable device may each be of various structures, as long as it is able to achieve the corresponding functions. A specific structure of each unit and an operating procedure thereof will be described hereinafter in more details. It should be appreciated that, each of the pulse detection circuitry 2, the identity determination circuitry 3 and the ECG detection circuitry 1 of the portable device may not be limited to the following structure.

Figure 3:
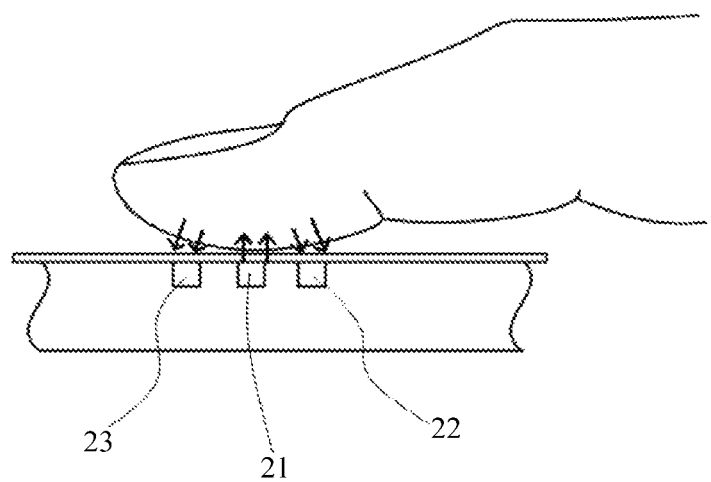
FIG. 3 is a schematic view showing a pulse detection circuitry according to one embodiment of the present disclosure.
Figure 5:
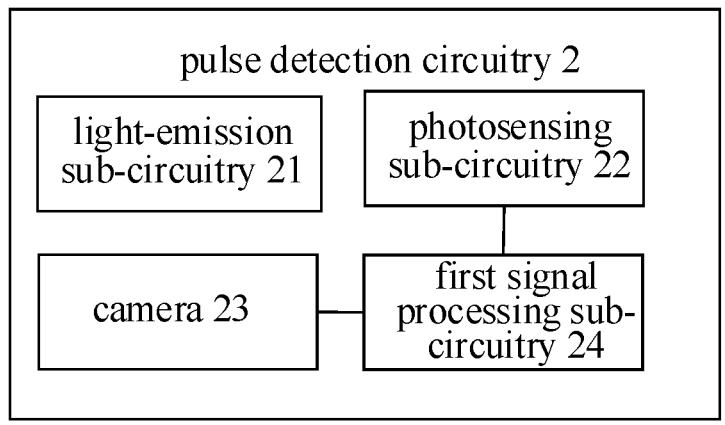
FIG. 5 is a block diagram of the pulse detection circuitry according to one embodiment of the present disclosure.

As shown in FIGS. 3 and 5, the pulse detection circuitry 2 includes a light-emission sub-circuitry 21, a photosensing sub-circuitry 22, and a first signal processing sub-circuitry 24.

The light-emission sub-circuitry 21 is configured to generate an initial light signal. To be specific, the light-emission sub-circuitry 21 may generate the initial light signal toward the user. A part of the initial light signal may be absorbed by the user, and the remaining light signal may be reflected by the user so as to form a reflected light signal. It should be appreciated that, the initial light signal generated by the light-emission sub-circuitry 21 may be of various types. In some embodiments of the present disclosure, the initial light signal may be a green light signal, a red light signal or an infrared light signal. In the case that the initial light signal generated by the light-emission sub-circuitry 21 is the green light signal, the red light signal or the infrared light signal, it may be absorbed by the user to a great extent after being irradiated onto the user, so it is able for the pulse detection circuitry 2 to provide a detection result in a more accurate manner.

The photosensing sub-circuitry 22 is configured to collect the reflected light signal formed after the initial light signal is reflected by the user. To be specific, in order to enable the photosensing sub-circuitry 22 to collect the reflected light signal formed after the initial light signal is reflected by the user in a more accurate manner, the photosensing sub-circuitry 22 may be arranged adjacent to the light-emission sub-circuitry 21. In some embodiments of the present disclosure, the photosensing sub-circuitry 22 and the light-emission sub-circuitry 21 are arranged within a range capable of being covered by a first knuckle of an adult's thumb. Therefore, during the measurement of the pulse wave signal of the user, both the photosensing sub-circuitry 22 and the light-emission sub-circuitry 21 may be covered by the first knuckle simultaneously, so that the photosensing sub-circuitry 22 may collect the reflected light signal in a more accurate manner. In addition, the photosensing sub-circuitry 22 may be a photosensitive sensor, so as to collected the reflected light signal in an accurate manner and transmit the reflected light signal being collected to the first signal processing sub-circuitry 24.

The first signal processing sub-circuitry 24 is connected to the photosensing sub-circuitry 22, and configured to process the reflected light signal, so as to acquire the pulse wave signal of the user.

To be specific, the first signal processing sub-circuitry 24 may be a pulse collection integrated circuit (IC) in the related art (e.g., ADPD142 opto-electronic IC from Analog Devices Inc., or analog front end (AFE) from Texas Instruments Inc.), which may process the reflected light signal being received, thereby to acquire the pulse wave signal of the user.

Figure 6:
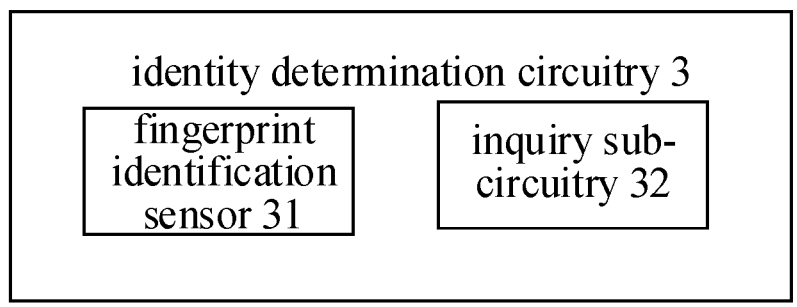
FIG. 6 is a block diagram of an identity determination circuitry according to one embodiment of the present disclosure.

As shown in FIG. 6, the identity determination circuitry 3 includes a fingerprint identification sensor 31 and an inquiry sub-circuitry 32.

The fingerprint identification sensor 31 is configured to determine fingerprint information about the user. To be specific, during the blood pressure measurement of the user through the portable device, a fingerprint of the user may be identified by the fingerprint identification sensor 31 so as to acquire the fingerprint information of the user, and then the fingerprint information may be transmitted to the inquiry sub-circuitry 32.

The inquiry sub-circuitry 32 is configured to inquire the identity information about the user in accordance with the fingerprint information of the user. To be specific, the respective pieces of fingerprint information and the respective pieces of identity information about different users may be stored in the portable device in advance, and each user may correspond to one respective piece of fingerprint information and one respective piece of identity information. During the blood pressure measurement of the user through the portable device, the inquiry sub-circuitry 32 may inquire the identity information about the user corresponding to the fingerprint information of the user currently identified by the fingerprint identification sensor 31 from the pre-stored respective pieces of identity information corresponding to the different users in accordance with the fingerprint information currently identified by the fingerprint identification sensor 31, and transmit the acquired identity information of the user to the blood pressure calculation circuitry 7.

Figure 2:
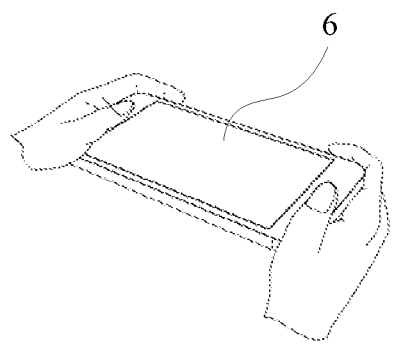
FIG. 2 is a schematic view showing the use of the portable device to measure a blood pressure according to one embodiment of the present disclosure.

As shown in FIG. 2, the portable device may be a mobile terminal 6. In the case that the portable device is the mobile terminal 6, a fingerprint identification button of the mobile terminal 6 may further serve as the fingerprint identification sensor 31, a flash lamp of the mobile terminal 6 may further serve as the light-emission sub-circuitry 21, and a camera 23 on the mobile terminal 6 may further serve as the photosensing sub-circuitry 22. In some embodiments of the present disclosure, the mobile terminal 6 may be a smart phone.

More specifically, most of the mobile terminals 6 in the related art are provided with a fingerprint identification function and a photographing function. Usually, the fingerprint identification function is achieved through the fingerprint identification button of the mobile terminal 6. In the case of performing the fingerprint identification by the user using the mobile terminal 6, the fingerprint information about the user may be recorded in the mobile terminal 6 through the fingerprint identification button in advance. Then, a finger whose fingerprint information has been recorded in the mobile terminal 6 may be in contact with the fingerprint identification button, so as to control the mobile terminal 6. The function of the fingerprint identification sensor 31 is identical to the function of the fingerprint identification button of the mobile terminal 6 in the related art, so it may enable the fingerprint identification button of the mobile terminal 6 to further serve as the fingerprint identification sensor 31. In this way, during the blood pressure measurement through the mobile terminal 6, it is able to record the fingerprint information about different users in a storage circuit of the mobile terminal 6 through the fingerprint identification button of the mobile terminal 6. The finger whose fingerprint information has already recorded in the mobile terminal may be in direct contact with the fingerprint identification button, so it is able to identify the fingerprint information of the user using the fingerprint identification button.

In addition, usually the mobile terminal 6 in the related art includes the camera 23 and the flash lamp. The flash lamp is capable of generating a light signal in a relatively dark photographing environment, so as to supplement light for the photographing environment. The camera 23 is capable of capturing the reflected light signal in the photographing environment, so as to achieve a photographing function of the mobile terminal. The function of the light-emission sub-circuitry 21 is identical to the function of the flash lamp of the mobile terminal 6 in the related art, and the function of the photosensing sub-circuitry 22 is identical to the function of the camera 23 on the mobile terminal 6 in the related art, so it may enable the flash lamp of the mobile terminal 6 to further serve as the light-emission sub-circuitry 21, and enable the camera 23 to further serve as the photosensing sub-circuitry 22. In this way, during the blood pressure measurement through the mobile terminal 6, it is able for the flash lamp of the mobile terminal 6 to generate the initial light signal, and for the camera 23 of the mobile terminal 6 to collect the reflected light signal formed after the initial light signal is reflected by the user.

It should be appreciated that, the photosensing sub-circuitry 22 may also be arranged on the mobile terminal 6, i.e., the reflected light signal may be collected by the photosensing sub-circuitry 22 and the camera 23 together, so as to collect the reflected light signal formed after the initial light signal is reflected by the user in a more accurate manner. In addition, in the case that the photosensing sub-circuitry 22 is arranged on the mobile terminal 6, the photosensing sub-circuitry 22 may be arranged adjacent to the flash lamp. In some embodiments of the present disclosure, the flash lamp may be arranged between the photosensing sub-circuitry 22 and the camera 23 in such a manner that the flash lamp, the photosensing sub-circuitry 22 and the camera 23 are capable of being covered by the first knuckle of the adult's thumb.

As mentioned above, in the case that the portable device is the mobile terminal 6, it is able for the user to carry the portable device conveniently. In addition, some elements of the mobile terminal 6 may further serve as the functional circuitries of the portable device, so it is able to reduce the number of the functional units of the mobile terminal 6, thereby to reduce the manufacture cost.

Figure 7:
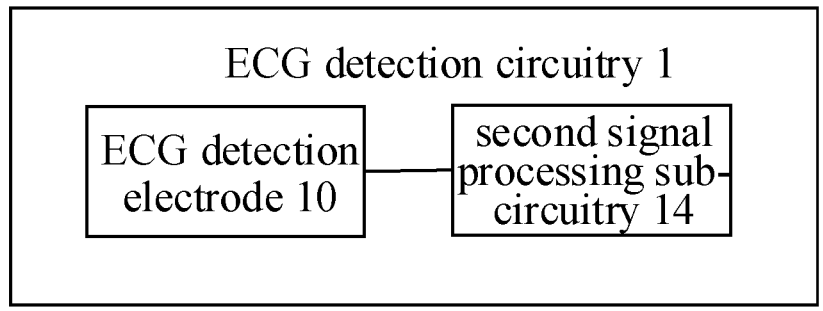
FIG. 7 is a block diagram of an ECG detection circuitry according to one embodiment of the present disclosure.

As shown in FIG. 7, the ECG detection circuitry 1 includes an ECG detection electrode 10 and a second signal processing sub-circuitry 14.

The ECG detection electrode 10 is arranged on the portable device, and configured to collect voltage signals corresponding to a left hand and a right hand of the user respectively. To be specific, the ECG detection electrode 10 may be a metal electrode. In the case that the portable device is used by the user, the left hand and the right hand of the user may be electrically connected to the ECG detection electrode 10. At this time, the ECG detection electrode 10 may collect the voltage signals corresponding to the left hand and the right hand of the user respectively.

The second signal processing sub-circuitry 14 is connected to the ECG detection electrode 10, and configured to process the voltage signals corresponding to the left hand and the right hand of the user, so as to acquire the ECG signal of the user. To be specific, the second signal processing sub-circuitry 14 may be a ECG collection IC in the related art (e.g., a high-precision analog to digital conversion IC ADS1292 form Texas Instruments Inc.), which may process the voltage signals corresponding to the left hand and the right hand of the user, thereby to acquire the ECG signal of the user.

It should be appreciated that, the structure and the arrangement mode of the ECG detection electrode 10 may be set in accordance with the practical need. In some embodiments of the present disclosure, the ECG detection electrode 10 and a housing of the portable device may be formed into one piece, i.e., the ECG detection electrode 10 may be formed as a part of the housing and exposed to the outside. In this way, during the blood pressure measurement of the user through the portable device, it is able for the ECG detection electrode 10 to collect the voltage signals corresponding to the left hand and the right hand of the user as long as the two hands are in contact with the ECG detection electrode 10. Alternatively, the ECG detection electrode 10 may be arranged inside the portable device and connected to different portions of the housing. In this arrangement mode, the portions of the housing connected to the ECG detection electrode 10 are capable of transmitting the voltage signals, and these different portions may be insulated from each other.

The ECG detection electrode 10 may include three ECG detection sub-electrodes that are insulated from each other. During the blood pressure measurement of the user through the portable device, one hand of the user may be in contact with two of the three ECG detection sub-electrodes at a contact area greater than or equal to 1 cm$^2$, and the other hand of the user may be in contact with the remaining ECG detection sub-electrode.

To be specific, for example, the three ECG detection sub-electrodes may include a first ECG detection sub-electrode 11, a second ECG detection sub-electrode 12 and a third ECG detection sub-electrode 13. During the blood pressure measurement of the user through the portable device, the left hand of the user may be in contact with the first ECG detection sub-electrode 11 and the second ECG detection sub-electrode 12, and the right hand of the user may be in contact with the third ECG detection sub-electrode 13. In this way, the voltage signal corresponding to the left hand of the user may be collected by the first ECG detection sub-electrode 11, a noise signal which interferes with the voltage signal may be collected by the second ECG detection sub-electrode 12, and the voltage signal corresponding to the right hand of the user may be collected by the third ECG detection sub-electrode 13. In order to enable the ECG detection sub-electrodes to collect the voltage signals corresponding to the left hand and the right hand of the user in an accurate manner, the ECG detection sub-electrodes 11-13 may be configured, such that the contact area between the left hand of the user and the two ECG detection sub-electrodes may be greater than or equal to 1 cm$^2$, and a contact area between the right hand of the user and the third ECG detection sub-electrode 13 may be greater than or equal to 0.5 cm$^2$. In this way, it is able for each of the ECG detection sub-electrodes to be in full contact with the left hand and the right hand of the user, thereby to collect the voltage signals in a more accurate manner. It should be appreciated that, alternatively, during the blood pressure measurement of the user through the portable device, the right hand of the user may be in contact with the first ECG detection sub-electrode 11 and the second ECG detection sub-electrode 12, and the left hand may be in contact with the third ECG detection sub-electrode 13.

Further, as shown in FIG. 2, in the case that the portable device is the mobile terminal 6, during the blood pressure measurement of the user through the portable device, two ends of the mobile terminal 6 may be held by the two hands of the user. At this time, the fingerprint identification button may be pressed by a thumb of one hand while the first ECG detection sub-electrode 11 and the second ECG detection sub-electrode 12 may be in contact with a forefinger of the one hand. At the same time, the light-emission sub-circuitry 21, the photosensing sub-circuitry 22 and the camera 23 may be shielded by a thumb of the other hand while the third ECG detection sub-electrode 13 may be in contact with a forefinger of the other hand. Alternatively, in the case that the two ends of the mobile terminal 6 are held by the two hands of the user, the fingerprint identification button may be pressed by a thumb of one hand while the first ECG detection sub-electrode 11 may be in contact with a forefinger of the one hand. At the same time, the light-emission sub-circuitry 21, the photosensing sub-circuitry 22 and the camera 23 may be shielded by a thumb of the other hand while the second ECG detection sub-electrode 12 and the third ECG detection sub-electrode 13 may be in contact with a forefinger of the other hand.

It should be appreciated that, in the case that the portable device is the mobile terminal 6, positions of the three ECG detection sub-electrodes may be set in accordance with the practical need, as long as one hand of the user is capable of being in contact with the two ECG detection sub-electrodes and the other hand is capable of being in contact with the remaining ECG detection sub-electrode during the blood pressure measurement of the user through the mobile terminal 6. For example, the three ECG detection sub-electrodes may be arranged in three segments of a frame of the mobile terminal 6, or arranged at a back of the mobile terminal 6.

As a result, it is able for the user to carry the portable device conveniently. In addition, during the blood pressure measurement of the user through the portable device, it is able for the user to operate the portable device in a simple manner, i.e., it enables the user to measure such physiological parameters as the ECG signal, the pulse wave signal and the blood pressure signal in a real-time manner merely by holding the portable device with two hands.

In different behavior models, the user's blood pressures may be different too. For example, the blood pressure of the user after strenuous exercise may be higher than a normal blood pressure value, so an inaccurate result may probably be acquired in the case that a health condition of the user is determined merely in accordance with the blood pressure signal measured by the portable device. In order to determine the health condition of the user in an accurate manner, the portable device may further include: a behavior pattern detection circuitry 4 connected to the blood pressure calculation circuitry 7, and configured to detect behavior pattern information about the user during the blood pressure measurement and transmit the behavior pattern information to the blood pressure calculation circuitry 7. The blood pressure calculation circuitry 7 is further configured to modify the blood pressure signal of the user in accordance with the behavior pattern information. To be specific, usually, the behavior pattern information about the user includes information indicating that the user is in a movement state, a sit-down state or a sleep state. Through detecting the behavior pattern information about the user during the measurement of the blood pressure using the behavior pattern detection circuitry 4 and modifying the blood pressure signal of the user using the blood pressure calculation circuitry 7 in accordance with the behavior pattern information, the portable device may determine the health condition of the user in accordance with the blood pressure signal in an accurate manner.

The behavior pattern detection circuitry may be of various types. In some embodiments of the present disclosure, a movement sensor may be selected as the behavior pattern detection circuitry and arranged inside the portable device. In the case that the portable device is being used by the user it is able for the movement sensor to further collect the current behavior pattern information about the user.

During the blood pressure measurement of the user through the portable device, the acquired blood pressure signal may be presented in various forms. In some embodiments of the present disclosure, the portable device may further include a display circuitry 5 configured to display the modified blood pressure signal of the user. In addition, in order to enable the user to determine the health condition in a comprehensive and accurate manner, the display circuitry 5 may be further configured to display the identity information, the ECG signal, the pulse wave signal and/or the behavior pattern information corresponding to the user.

Through displaying the identity information, the modified blood pressure signal, the ECG signal, the pulse wave signal and the behavior pattern information corresponding to the user by the display circuitry 5, it is able for the user to view the measured parameters conveniently and determine the health condition in a more accurate manner in accordance with these parameters.

The identity information, the modified blood pressure signal, the ECG signal, the pulse wave signal and the behavior pattern information about the user may also be stored in the portable device or uploaded to a server for the user's reference during the subsequent blood pressure measurement.

Figure 4:
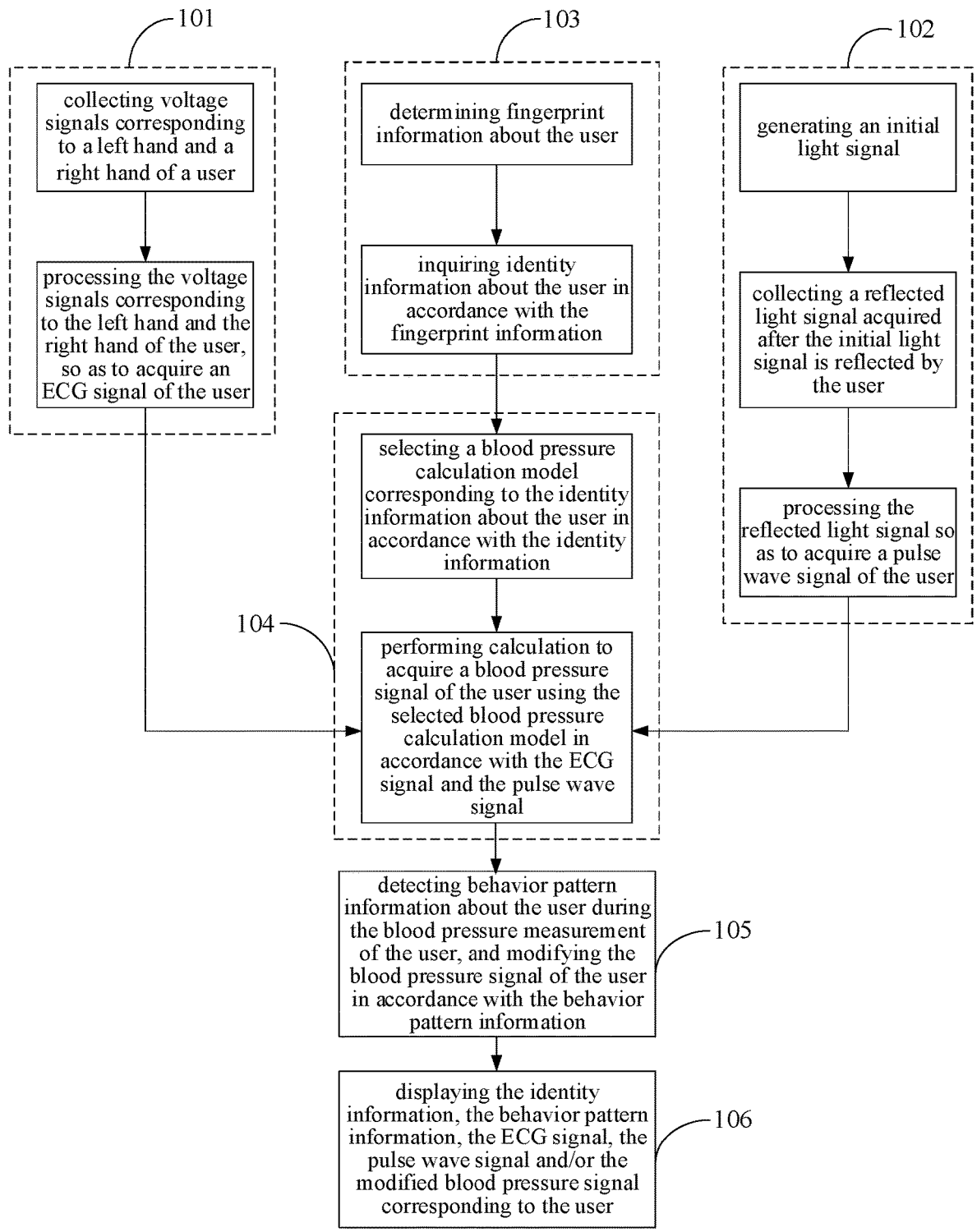
FIG. 4 is a flow chart of a blood pressure measurement method according to one embodiment of the present disclosure.

The present disclosure further provides in some embodiments a blood pressure measurement method for use in the above-mentioned portable device. As shown in FIG. 4, the blood pressure measurement method includes the following steps.

Step 101: detecting the ECG signal of the user. To be specific, the voltage signals corresponding to the left hand and the right hand of the user may be collected through the ECG detection electrode of the portable device, and then the voltage signals corresponding to the left hand and the right hand of the user may be processed through the second signal processing sub-circuitry of the portable device, so as to acquire the ECG signal of the user.

Step 102: detecting the pulse wave signal of the user. To be specific, the initial light signal may be generated by the light-emission sub-circuitry of the portable device, and the reflected light signal formed after the initial light signal is reflected by the user may be collected by the photosensing sub-circuit of the portable device and then processed by the first signal processing sub-circuitry of the portable device, so as to acquire the pulse wave signal of the user.

Step 103: determining the identity information about the user. To be specific, the fingerprint information about the user may be determined through the fingerprint identification sensor of the portable device, and then the identity information about the user may be inquired by the inquiry sub-circuitry of the portable device in accordance with the fingerprint information of the user.

Step 104: selecting the blood pressure calculation model corresponding to the identity information in accordance with the identity information, and performing calculation to acquire the blood pressure signal of the user using the selected blood pressure calculation model in accordance with the ECG signal and the pulse wave signal. To be specific, the blood pressure calculation model corresponding to the identity information about the user may be selected by the blood pressure calculation circuitry of the portable device from the pre-stored blood pressure calculation models in accordance with the identity information about the user, and the ECG signal and the pulse wave signal may be substituted into the selected blood pressure calculation model, so as to acquire the blood pressure signal of the user.

In a possible embodiment of the present disclosure, the blood pressure calculation model may be:

$$BP = f(x,y) * h(a,b,c,d) \quad (1),$$

where BP represents the blood pressure signal of the user, x represents the ECG signal of the user, y represents the pulse wave signal of the user, a represents gender of the user, b represents an age of the user, c represents a height of the user, and d represents a weight of the user.

According to the blood pressure measurement method in the embodiments of the present disclosure, the identity information about the user is determined at first, and then the blood pressure calculation model corresponding to the identity information is selected in accordance with the identity information. The blood pressure signal of the user is calculated in accordance with the ECG signal and the pulse wave signal using the selected blood pressure calculation model. As a result, it is able to measure the blood pressure at any time and at any place if required. In addition, it is able to select the respective blood pressure calculation models corresponding to different users, thereby to provide a blood pressure detection result in a more accurate manner.

In addition, in the case that the ECG detection electrode and the housing of the portable device are formed into one piece, and the ECG detection electrode includes three ECG detection sub-electrodes insulated from each other, the step of detecting the ECG signal of the user during the blood pressure measurement of the user through the portable device may include: enabling one hand of the user to be in contact with two of the three ECG detection sub-electrodes at a contact area greater than or equal to 1 cm$^2$, so as to enable the two ECG detection sub-electrodes to collect the voltage signal corresponding to the hand and a noise signal interfering with the voltage signal respectively; and enabling the other hand of the user to be in contact with the remaining one ECG detection sub-electrode at a contact area of greater than or equal to 0.5 cm$^2$, so as to enable the remaining one ECG detection sub-electrode to collect the voltage signal corresponding to the other hand.

In a possible embodiment of the present disclosure, the blood pressure measurement method further includes: Step 105 of detecting the behavior pattern information about the user during the blood pressure measurement of the user through the portable device, and modifying the blood pressure signal of the user in accordance with the behavior pattern information.

To be specific, usually the behavior pattern information includes information indicating that the user is in a movement state, a sit-down state or a sleep state. Through detecting the behavior pattern information about the user during the blood pressure measurement, it is able to modify the blood pressure signal in accordance with the behavior pattern information after the blood pressure signal of the user is acquired, thereby to determine the health condition of the user in accordance with the blood pressure signal in a more accurate manner.

More specifically, in the case that the behavior pattern information of the user during the blood pressure measurement of the user has been detected, the modified blood pressure signal BP' may be calculated using the following equation:

$$BP' = e * BP + f \quad (2),$$

where e and f represent modification coefficients acquired in accordance with the behavior pattern information of the user during the blood pressure measurement, and the other parameters have meanings identical to those in equation (1).

In a possible embodiment of the present disclosure, the blood pressure measurement method may further include Step 106 of displaying the behavior pattern information, the modified ECG signal, the pulse wave signal, the identity information and the blood pressure signal corresponding to the user.

Through displaying the identity information, the modified blood pressure signal, the ECG signal, the pulse wave signal and/or the behavior pattern information corresponding to the user by the display circuitry of the portable device, it is able for the user to view the measured parameters conveniently and determine the health condition in a more accurate manner in accordance with these parameters.

It should be appreciated that, the features, structures, materials or characteristics hereinabove may be combined in any embodiment(s) in an appropriate manner.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure. A protection scope of the present disclosure is defined by the attached claims.

What is claimed is:

1. A portable device, wherein the portable device is a smart phone configured to be used by a user to measure a blood pressure of the user, the portable device comprising:
   an electrocardiogram (ECG) detection circuitry configured to detect an ECG signal of a user;
   a pulse detection circuitry configured to detect a pulse wave signal of the user;
   an identity determination circuitry configured to determine identity information about the user; and
   a blood pressure calculation circuitry connected to each of the ECG detection circuitry, the pulse detection circuitry and the identity determination circuitry, wherein the blood pressure calculation circuitry is configured to store therein a plurality of blood pressure calculation models, select a blood pressure calculation model corresponding to the identity information about the user among the plurality of blood pressure calculation models in accordance with the identity information, and perform calculation to acquire a blood pressure signal of the user using the selected blood pressure calculation model in accordance with the ECG signal and the pulse wave signal, wherein the ECG detection circuitry comprises:
an ECG detection electrode arranged on the portable device, and configured to collect voltage signals corresponding to a left hand and a right hand of the user respectively; and
a second signal processing sub-circuitry connected to the ECG detection electrode, and configured to process the voltage signals corresponding to the left hand and the right hand of the user respectively, to acquire the ECG signal of the user,
wherein the ECG detection electrode and a housing of the portable device are formed into one piece;
the ECG detection electrode consists of a first ECG detection sub-electrode, a second ECG detection sub-electrode, and a third ECG detection sub-electrode that are insulated from each other, the housing of the portable device comprises a top lateral portion, a bottom lateral portion, a left lateral portion, and a right lateral portion, the top lateral portion is opposite to the bottom lateral portion, the left lateral portion is opposite to the right lateral portion, the first ECG detection sub-electrode and one of the top lateral portion and the bottom lateral portion are formed into one piece, the third ECG detection sub-electrode and the other one of the top lateral portion and the bottom lateral portion are formed into one piece, the second ECG detection sub-electrode and one of the left lateral portion and the right lateral portion are formed into one piece, the first ECG detection sub-electrode is configured to collect the voltage signal corresponding to one hand of the user, the second ECG detection sub-electrode is configured to collect a noise signal interfering with the voltage signal corresponding to the one hand of the user, and the third ECG detection sub-electrode is configured to collect the voltage signal corresponding to the other hand of the user; and
the first and second ECG detection sub-electrodes are further configured to be contacted by the one hand of the user at a contact area greater than or equal to 1 cm$^2$, and the third ECG detection sub-electrode is further configured to be contacted by the other hand of the user when the portable device is used by the user to measure a blood pressure.

2. The portable device according to claim 1, wherein the pulse detection circuitry comprises:
a light-emission sub-circuitry configured to generate an initial light signal;
a photosensing sub-circuitry configured to collect a reflected light signal formed by the initial light signal reflected by the user; and
a first signal processing sub-circuitry connected to the photosensing sub-circuitry, and configured to process the reflected light signal to acquire the pulse wave signal of the user.

3. The portable device according to claim 2, wherein the identity determination circuitry comprises:
a fingerprint identification sensor configured to determine fingerprint information about the user; and
an inquiry sub-circuitry configured to inquire the identity information about the user in accordance with the fingerprint information about the user.

4. The portable device according to claim 3, wherein the portable device is a mobile terminal, a fingerprint identification button of the mobile terminal serves as the fingerprint identification sensor, a flash lamp of the mobile terminal serves as the light-emission sub-circuitry, and a camera of the mobile terminal serves as the photosensing sub-circuitry.

5. The portable device according to claim 2, wherein the initial light signal is a green light signal, a red light signal or an infrared light signal.

6. The portable device according to claim 1, further comprising:
a behavior pattern detection circuitry connected to the blood pressure calculation circuitry, and configured to detect behavior pattern information about the user during measurement of blood pressure of the user;
wherein the blood pressure calculation circuitry is further configured to modify the blood pressure signal of the user in accordance with the behavior pattern information.

7. The portable device according to claim 6, wherein the behavior pattern detection circuitry comprises a movement sensor arranged inside the portable device.

8. The portable device according to claim 6, wherein the behavior pattern information comprises information indicating that the user is in a movement state or a sit-down state during the measurement of the blood pressure.

9. The portable device according to claim 6, further comprising:
a display circuitry configured to display the behavior pattern information, the ECG signal, the pulse wave signal, the identity information and/or the modified blood pressure signal.

10. The portable device according to claim 1, wherein
the blood pressure calculation model is BP=f(x,y)*h(a,b,c,d), where BP represents the blood pressure signal of the user, x represents the ECG signal of the user, y represents the pulse wave signal of the user, a represents gender of the user, b represents an age of the user, c represents a height of the user, and d represents a weight of the user.

11. A blood pressure measurement method comprising:
providing the portable device according to claim 1;
detecting, by the portable device, the ECG signal of the user;
detecting, by the portable device, the pulse wave signal of the user;
determining, by the portable device, the identity information about the user; and
selecting, by the portable device, the blood pressure calculation model corresponding to the identity information about the user according to the identity information, and performing, by the portable device, calculation to acquire the blood pressure signal of the user using the selected blood pressure calculation model in accordance with the ECG signal and the pulse wave signal.

12. The blood pressure measurement method according to claim 11, wherein
the blood pressure calculation model is BP=f(x,y)*h(a,b,c,d), where BP represents the blood pressure signal of the user, x represents the ECG signal of the user, y represents the pulse wave signal of the user, a represents gender of the user, b represents an age of the user, c represents a height of the user, and d represents a weight of the user.

* * * * *